United States Patent
Liu et al.

(10) Patent No.: US 12,122,992 B2
(45) Date of Patent: Oct. 22, 2024

(54) LARGE-FLUX IN-SITU FILTRATION DEVICES FOR MARINE MICROORGANISM BASED ON MULTI-CHANNEL CIRCULATION DISTRIBUTORS

(71) Applicant: ZHEJIANG UNIVERSITY, Zhejiang (CN)

(72) Inventors: Shuo Liu, Zhoushan (CN); Zhiyong Sun, Zhoushan (CN); Yu Zhang, Zhoushan (CN); Shanmin Zhou, Zhoushan (CN); Jingyang Li, Zhoushan (CN); Yang Shi, Zhoushan (CN); Yong Cai, Zhoushan (CN); Jiwei Tian, Zhoushan (CN); Xiao Zhang, Zhoushan (CN); Yu Xin, Zhoushan (CN)

(73) Assignee: ZHEJIANG UNIVERSITY, Zhoushan (CN)

( * ) Notice: Subject to any disclaimer, the term of this patent is extended or adjusted under 35 U.S.C. 154(b) by 92 days.

(21) Appl. No.: 18/180,084

(22) Filed: Mar. 7, 2023

(65) Prior Publication Data

US 2023/0287323 A1 Sep. 14, 2023

(30) Foreign Application Priority Data

Mar. 10, 2022 (CN) .......................... 202210231845.6

(51) Int. Cl.
*C12M 1/00* (2006.01)
*C02F 1/00* (2023.01)
(Continued)

(52) U.S. Cl.
CPC ............ *C12M 33/14* (2013.01); *C12M 23/48* (2013.01); *C12M 41/22* (2013.01); *C12M 41/44* (2013.01); *C12M 41/48* (2013.01)

(58) Field of Classification Search
CPC ......... C12M 41/48; C12M 33/14; C02F 1/001
See application file for complete search history.

(56) References Cited

U.S. PATENT DOCUMENTS

| 6,432,304 B1 * | 8/2002 | Nguyen | .................. B63B 13/02 |
| | | | 210/931 |
| 2009/0218297 A1 * | 9/2009 | Glessner | ................. B63B 13/02 |
| | | | 210/162 |

(Continued)

FOREIGN PATENT DOCUMENTS

| CN | 105420097 A | 3/2016 |
| CN | 107937249 A | 4/2018 |

(Continued)

OTHER PUBLICATIONS

Notification to Grant Patent Right for Invention in Chinese Application No. 202210231845.6 mailed on May 14, 2024, 6 pages.

*Primary Examiner* — Nathan A Bowers
(74) *Attorney, Agent, or Firm* — METIS IP LLC

(57) ABSTRACT

A large-flux in-situ filtration device for marine microorganism based on a multi-channel circulation distributor is provided, comprising an energy and control module, a circulation distribution module, a filtration module, a pump module, a filtration volume measurement module, a pipeline connection, and a main body support frame. The circulation distribution module may include a multi-channel circulation distributor, a deep-sea servo motor, etc. The filtration module may include a plurality of filter film holders. The pump module may include a stainless steel gear pump, a deep-sea drive motor, etc. The filtration volume measurement module may include a water meter, a camera, and an LED light.

8 Claims, 10 Drawing Sheets

(51) Int. Cl.
*C12M 1/02* (2006.01)
*C12M 1/26* (2006.01)
*C12M 1/34* (2006.01)
*C12M 1/36* (2006.01)
*C12M 3/00* (2006.01)

(56) References Cited

U.S. PATENT DOCUMENTS

2012/0202274 A1\* 8/2012 Yancey, Jr. ............ C12M 23/18
　　　　　　　　　　　　　　　　　　　　　　　435/297.1
2022/0112096 A1\* 4/2022 Rodriguez-Vilches ......................
　　　　　　　　　　　　　　　　　　　　　　　C02F 1/008

FOREIGN PATENT DOCUMENTS

CN　　109187104　A　　1/2019
CN　　209854124　U　　12/2019

\* cited by examiner

LARGE-FLUX IN-SITU FILTRATION DEVICES FOR MARINE MICROORGANISM BASED ON MULTI-CHANNEL CIRCULATION DISTRIBUTORS

CROSS-REFERENCE TO RELATED APPLICATIONS

This application claims the priority of Chinese Patent Application No. 202210231845.6, filed on Mar. 10, 2022, the entire contents of which are hereby incorporated herein by reference in its entirety.

TECHNICAL FIELD

The present disclosure relates to the field of marine microorganism collection technology, and in particular, to large-flux in-situ filtration devices for marine microorganism based on multi-channel circulation distributors.

BACKGROUND

The unique metabolic pathways, metabolites and gene types of marine microorganism are of great scientific value. In recent years, more and more studies have been conducted on the community composition and gene functions of deep-sea microorganism. However, the microorganism may be sparse in the ocean, and the study of metagenomics and metatranscriptomes may require microbial samples with sufficient biomass for processing and analysis.

The conventional way of obtaining marine microorganism may be as follows: a CTD water sampler may collect seawater and then filter it on the deck. This method may be time-consuming and laborious for metagenomic study, and may cause pollution during the deck filtration process. Therefore, it may be very necessary to carry out large-flux in-situ filtration of microorganism, to realize high-density sampling of microorganism in situ in the deep sea, and provide sufficient samples for laboratories to carry out subsequent genomics research work. Although some in-situ filtration sampling equipment for marine microorganism have been developed at home and abroad in recent years, such as Large Volume Water Transfer System, McLane (WTS-LV), one device may only collect a set of samples, and the amount of organisms obtained per deployment is still relatively small.

SUMMARY

Based on the above problems, the present disclosure provides a large-flux in-situ filtration device for marine microorganism based on a multi-channel circulation distributor. When the device performs in-situ filtration for the marine microorganism, the multi-channel circulation distributor may be driven by the deep-sea servo motor to switch the flow channel after the completion of filtration of one set of filter films, and the filtration of the next set of filter films may be continued. A plurality of sets of samples may be obtained through one deployment, thereby obtaining large-flux marine microbial samples.

In order to achieve the above purpose, the following technical solutions of the present disclosure may be adopted.

The present disclosure provides a large-flux in-situ filtration device for marine microorganism based on a multi-channel circulation distributor. According to the system level, the device may include an energy and control module, a circulation distribution module, a filtration module, a pump module, a filtration volume measurement module, a pipeline connection, and a main body support frame.

The energy and control module may include an electronic compartment, and a battery compartment.

The circulation distribution module may include a multi-channel circulation distributor, a deep-sea servo motor, and a hydraulic device.

The filtration module may include a plurality of filter film holders, such as eight filter film holders, or the like.

The pump module may include a stainless steel gear pump and a deep-sea drive motor.

The filtration volume measurement module may include a water meter, a camera, and a light emitting diode (LED) light.

The pipeline connection may be as follows: an inlet of the stainless steel gear pump may be connected to a seawater inlet, an outlet of the stainless steel gear pump may be connected to a pipe connection at a center above the multi-channel circulation distributor, and a plurality of pipe connections below a side of the multi-channel circulation distributor may be respectively connected to inlets of the plurality of filter film holders, and an outlet of each of the plurality of filter film holders may be connected to an inlet of the water meter through a multi-way pipe joint, and an outlet of the water meter may be an outlet of the device.

The energy and control module may adopt a radial sealing mode. Watertight connectors may be provided on an outer shell of a compartment body, which may be connected to the deep-sea servo motor, the deep-sea drive motor, the camera, the LED light, and other components through water-tight cables to provide power and automatic control for the components.

The circulation distribution module may include the multi-channel circulation distributor and the deep-sea servo motor. The multi-channel circulation distributor and the deep-sea servo motor may be connected to a shaft sleeve through a coupling. The multi-channel circulation distributor may specifically include a plurality of pipe joints, an upper cover plate, a rotor, an outer shell, a spacer column, a transmission connection shaft, a lower cover plate, a polytetrafluoroethylene (PTFE) gasket, and an O-shaped rubber ring. A center of the upper cover plate may be connected to an outlet the stainless steel gear pump by the pipe joint. A side of the lower cover plate may include eight pipe joints and an initial sealing position. The eight pipe joints and the initial sealing position may be evenly distributed in a circular array, and a difference between each adjacent two positions is 40 degrees. The eight pipe joints may be respectively connected to inlets of the filter film holders. An inside of the rotor may be provided with a unique water passage. One end of the water passage may be connected to a central water outlet of the upper cover, and other end of the water passage may be sequentially connected to eight water holes inside the lower cover when the rotor rotates for one cycle. The upper cover plate, the outer shell, and the lower cover plate may be fixed together to form a stator through screws. The rotor may be located in an inner space of the stator. The rotor may be fastened to the transmission connection shaft through screws, and then connected to the deep-sea servo motor through the coupling. The shaft sleeve may be wrapped on an outside of the coupling to fixedly connect the lower cover plate and a shell body of the deep-sea servo motor. The deep-sea servo motor may have the characteristics of high torque and low speed, and may realize position control through encoder feedback, so as to complete precise channel switching and connection when driving the rotor to rotate.

A joint surface between the rotor and the stator (the upper cover plate, the outer shell, and the lower cover plate) inside the multi-channel circulation distributor may all be coated with a novel corrosion-resistant and wear-resistant material to reduce rotational friction. During design and processing, the outer shell surrounding the rotor may be 0.1-0.2 mm higher than the rotor. A joint surface of the rotor and the upper or lower cover plates may be provided with PTFE spacer columns for keeping a space. The multi-channel circulation distributor may be made of a 316 stainless steel. The PTFE spacer column may be distributed on the joint surface of the rotor and the upper or lower cover plates in a circular array and may be 0.05-0.15 mm higher than a surface of the upper or lower cover plates, to ensure smooth rotation of the rotor. A joint surface of the rotor and the upper or lower cover plates is provided with a PTFE spacer column for keeping a space, and the space is within a range of 0.05-0.1 mm.

A seawater channel at a joint surface between the rotor and the lower cover plate may be sealed with an O-shaped PTFE gasket and the O-shaped rubber ring. The O-shaped rubber ring may be located at a bottom of a groove and used for compensating a space at the joint surface using self-elasticity of the O-shaped rubber ring to reduce a seawater leakage. The PTFE gasket may be placed above the O-shaped rubber ring and may be close to a surface of the rotor to realize sliding sealing.

The filtration module may include a plurality of filter film holders, which may be distributed around the multi-channel circulation distributor in a circular array. The filter film holders may all be stainless steel disc single-layer flat filters, each of which may include upper and lower cover plates and a threaded mesh plate in the middle. During use, the upper and lower cover plates may be fixed through 4-8 set screws and the mesh plate may be clamped. Filter films may be stored on the mesh plate as microporous film pressure support surfaces, to ensure that the filter films may not be liable to break under the filtration pressure. Obviously, more filter film holders may be arranged to increase the filtration flux. More filter film holders may be connected by reducing an angle between the adjacent pipe joints on the lower cover plate of the multi-channel circulation distributor and increasing the number of connection joints on the lower cover plate.

The pump module may include the stainless steel gear pump and the deep-sea drive motor. The stainless steel gear pump and the deep-sea drive motor may be connected through a coupling. An outside of the coupling may be fixed by the shaft sleeve. The deep-sea driver motor may adopt speed loop and power loop control, and a speed of the deep-sea driver motor may be adjustable.

The filtration volume measurement module may measure a volume of filtered seawater using a water meter, and display the volume of filtered seawater on a dial. When the LED light provides a light source, the camera may automatically photograph and record data of the volume of filtered seawater corresponding to each set of samples.

The main body support frame may be composed of a large frame and a small frame, providing installation of all parts of the device. The large frame may be cylindrical, the small frame may be cuboid, and the small frame may be pushed into the large frame and fixed with bolts. The circulation distribution module may be installed at a center of the small frame. The filter film holders in the filtration module may be installed on the small frame around the multi-channel circulation distributor in a circular array. A certain space may be left between the circulation distribution module and the filtration module to carry out installation of the pump module. The energy and control module and the filtration volume measurement module may be installed on the large frame and fixed by hoops.

After the in-situ filtration device is deployed in the ocean, the stainless steel gear pump may start to run, and the seawater may be pressed into the multi-channel circulation distributor through the stainless steel gear pump to enter the filter film holders. The filter films may be arranged in the filter film holders, which may enrich and filter the seawater microorganism flowing through the filter films. The filtered seawater may flow out of the device through the water meter. After the filtration of the filter films is completed, the energy and control module may drive the multi-channel circulation distributor to switch the flow channel, connect to the unused filter film holder, and start filtering again after reaching a preset condition, thereby obtaining a plurality of sets of samples in one deployment. The volume of seawater samples filtered by each filter film holder may be recorded by the filtration volume measurement module.

In some preferable embodiments, the device may further include two pressure sensors, which are respectively installed at an inlet and an outlet of the multi-channel circulation distributor. The two pressure sensors may be configured to detect a pressure at both ends of the multi-channel circulation distributor. The energy and control module may control a driving force of the stainless-steel gear pump through the pressure.

In some preferable embodiments, the device may further include a primary filter, which is installed at an inlet of the device to prevent small organisms and large particles from being sucked into the device and causing damage or blockage of the filter films.

In some preferable embodiments, the device may further include a temperature-salt-depth sensor, which is fixed on the main body support frame and connected to the energy and control module using a watertight cable to obtain basic background data of an in-situ sampling.

In some preferable embodiments, the device may further includes include an underwater acoustic communicator, which is fixed on the main body support frame and connected to the energy and control module using a watertight cable. The underwater acoustic communicator may realize a data transmission between the device and a host computer during a sampling process.

In some embodiments, an outside of the filter film frame may be provided with a shell body. A piston end cover may be fitted on the shell body. The piston end cover may be connected to a hydraulic rod of a hydraulic device inside the shell body. The hydraulic rod may be configured to control a position of the end cover in the shell body to apply pressure to a liquid environment inside the shell body through the end cover. An inner wall of the shell body may be provided with an internal temperature-salt-depth sensor. The internal temperature-salt-depth sensor may be configured to monitor at least one of an internal temperature, an internal pressure, and electrical conductivity information of the shell body. Detection data of the internal temperature-salt-depth sensor may be regularly transmitted back to the host computer through the underwater acoustic communicator for storage. A temperature adjustment device may be provided outside the shell body. The temperature adjustment device may include a copper pipe arranged around the shell body. The temperature adjustment device may be configured to adjust the internal temperature of the shell body. The energy and control module may be further configured to control the hydraulic device in the shell body to apply the pressure to the end cover.

In some embodiments, the energy and control module may be further configured to control the pressure applied by the hydraulic device on the end cover to keep a stability of the internal pressure of the shell body based on the internal pressure of the shell body and a seawater pressure.

In some embodiments, the temperature adjustment device may be further configured to adjust the internal temperature of the shell body to keep the stability of the internal temperature of the shell body based on the internal temperature of the shell body and the seawater temperature.

In some embodiments, the temperature adjustment device may be further configured to obtain an external temperature of the shell body; determine a target temperature range based on the seawater temperature when collecting microbial samples; periodically predict the internal temperature of the shell body in a plurality of future time periods based on the external temperature of the shell body; determine a temperature adjustment time node based on the internal temperature of the shell body and the target temperature range in the plurality of future time periods; and evaluate the seawater temperature at the temperature adjustment time node and the seawater temperature during a time period before the temperature adjustment time node, and determine a temperature adjustment mode corresponding to the temperature adjustment time node based on the seawater temperature, the temperature adjustment mode including at least one of a seawater flushing adjustment and a power device adjustment.

In some embodiments, the temperature adjustment device may be further configured to, for each of the plurality of future time periods, predict the internal temperature of the shell body when the time period ends through a temperature prediction model based on an initial internal temperature of the shell body and the external temperature of the shell body in the time period, and a duration of the time period, the temperature prediction model being a machine learning model.

In some embodiments, the temperature adjustment device may be further configured to determine whether the internal temperature of the shell body exceeds the target temperature range at the end of the time period; in response to a determination that the internal temperature of the shell body exceeds the target temperature range, take an end time point of the time period as a target time point and obtain a real-time seawater temperature; determine whether the real-time seawater temperature meets a reverse water temperature requirement; in response to a determination that the real-time seawater temperature meets the reverse water temperature requirement, adjust the internal temperature of the shell body by the seawater flushing adjustment until the internal temperature of the shell meets a first preset condition; in response to a determination that the real-time seawater temperature does not meet the reverse water temperature requirement, and when a difference between a current time point and the target time point meets a second preset condition, adjust the internal temperature of the shell body by the power device adjustment until the internal temperature of the shell body meets the first preset condition; take the internal temperature of the shell body that meets the first preset condition as the initial internal temperature of the shell body, predict the internal temperature of the shell body when reaching a target duration in combination with the external temperature of the shell body and the target duration through the temperature prediction model; and determine again whether the internal temperature of the shell body exceeds the target temperature range and repeat the aforementioned operations.

BRIEF DESCRIPTION OF THE DRAWINGS

The present disclosure will be further illustrated by way of exemplary embodiments, which will be described in detail with the accompanying drawings. These embodiments are non-limiting. In these embodiments, the same count indicates the same structure, wherein.

DETAILED DESCRIPTION

The following will clearly and completely describe the technical solutions in the embodiments of the present disclosure with reference to the accompanying drawings in the embodiments of the present disclosure. Obviously, the described embodiments are only some embodiments of the present disclosure. Based on the embodiments of the present disclosure, all other embodiments obtained by those having ordinary skill in the art, without creative efforts, belong to the protection scope of the present disclosure.

Figure 1:
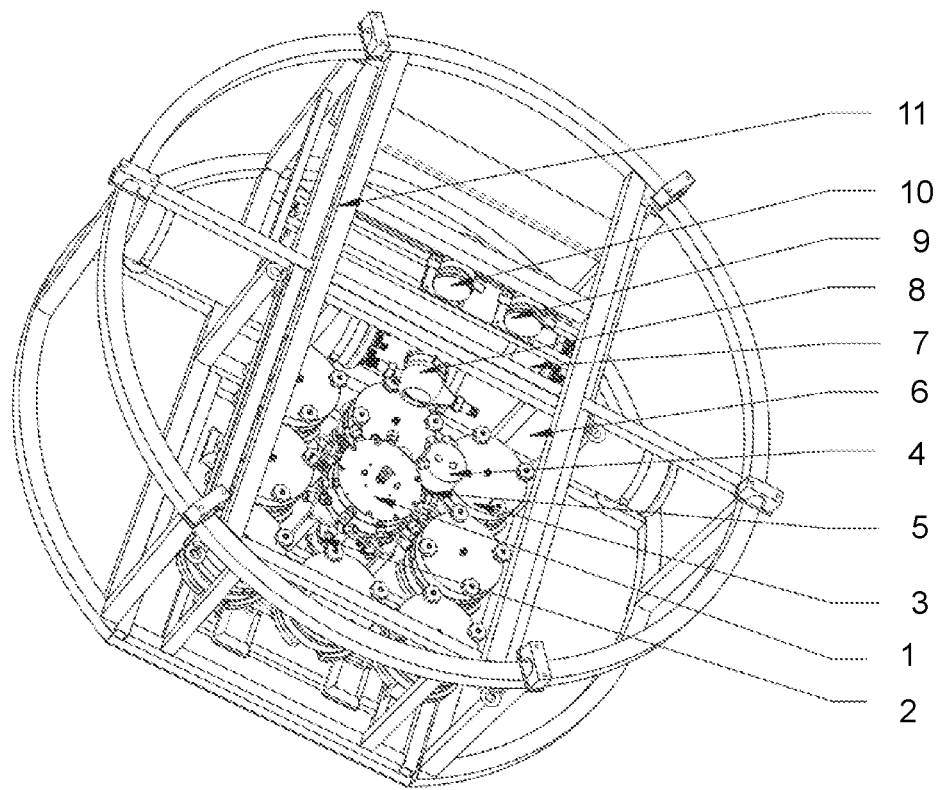
FIG. 1 is a schematic diagram illustrating an assembly structure of a large-flux in-situ filtration device for marine microorganism based on a multi-channel circulation distributor according to some embodiments of the present disclosure.

Referring to FIG. 1, a large-flux in-situ filtration device for marine microorganism based on a multi-channel circulation distributor may include a multi-channel circulation distributor 1, a deep-sea servo motor 2, filter film holders 3, a stainless steel gear pump 4, a deep-sea drive motor 5, a battery compartment 6, an electronic compartment 7, a water meter 8, a camera 9, a light emitting diode (LED) light 10, and a main body support frame 11.

In some embodiments, according to the system level, the device may include an energy and control module, a circulation distribution module, a filtration module, a pump module, a filtration volume measurement module, a pipeline connection, and the main body support frame 11. The main body support frame 11 may be composed of a large frame and a small frame, providing installation of all parts of the device. The large frame may be cylindrical, the small frame may be cuboid, and the small frame may be pushed into the large frame and fixed with bolts. The circulation distribution module may be installed at a center of the small frame. The filtration module may be installed on the small frame around the multi-channel circulation distributor in a circular array. A certain space may be left between the circulation distribution module and the filtration module for installation of the pump module. The energy control module and the filtration volume measurement module may be installed on the large frame and fixed by hoops.

Figure 2:
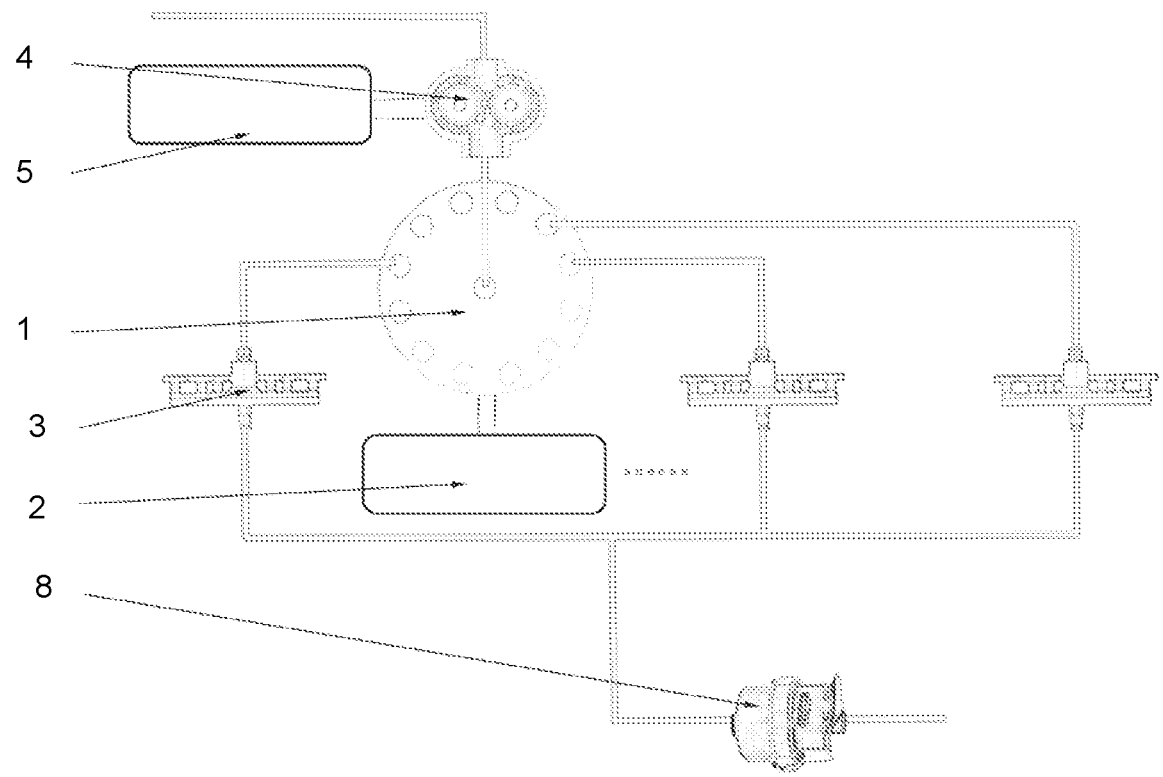
FIG. 2 is a schematic diagram illustrating a pipeline connection principle of a large-flux in-situ filtration device for marine microorganism based on a multi-channel circulation distributor according to some embodiments of the present disclosure.

According to FIG. 2, in some embodiments, the pipeline connection may be as follows: an inlet of the stainless steel gear pump 4 may be connected to a seawater inlet, and an outlet of the stainless steel gear pump 4 may be connected to a pipe connection 12 at a center of the upper cover plate 13 of the multi-channel circulation distributor 1 and connected with a pipe joint of a side of the lower cover plate 18 of the multi-channel circulation distributor 1 through a seawater flow channel in the rotor 14 inside the multi-channel circulation distributor 1. Pipe joints of a side of the lower cover plate 18 may be respectively connected to the inlets of the plurality of filter film holders 3. The outlet of each of the plurality of filter film holders may be connected to an inlet of the water meter 8 through a multi-way pipe joint, and an outlet of the water meter may be an outlet of the device.

In some embodiments, the energy and control module may include the electronic compartment 6 and the battery compartment 7, and adopt a radial sealing mode. Watertight connectors may be provided on an outer shell of the compartment, and connected to the deep-sea servo motor 2, the deep-sea drive motor 5, the camera 9, the LED light 10 and other components to provide power and automatic control for the components.

Figure 3A:
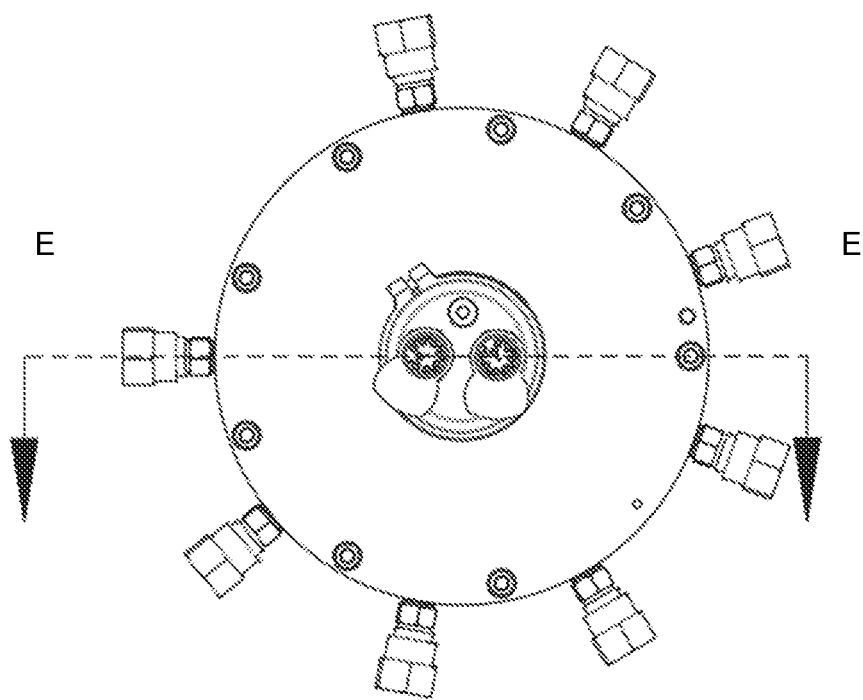
FIG. 3a and FIG. 3b are schematic diagrams illustrating sectional structures of a circulation distribution module of a large-flux in-situ filtration device for marine microorganism based on a multi-channel circulation distributor according to some embodiments of the present disclosure.
Figure 3B:
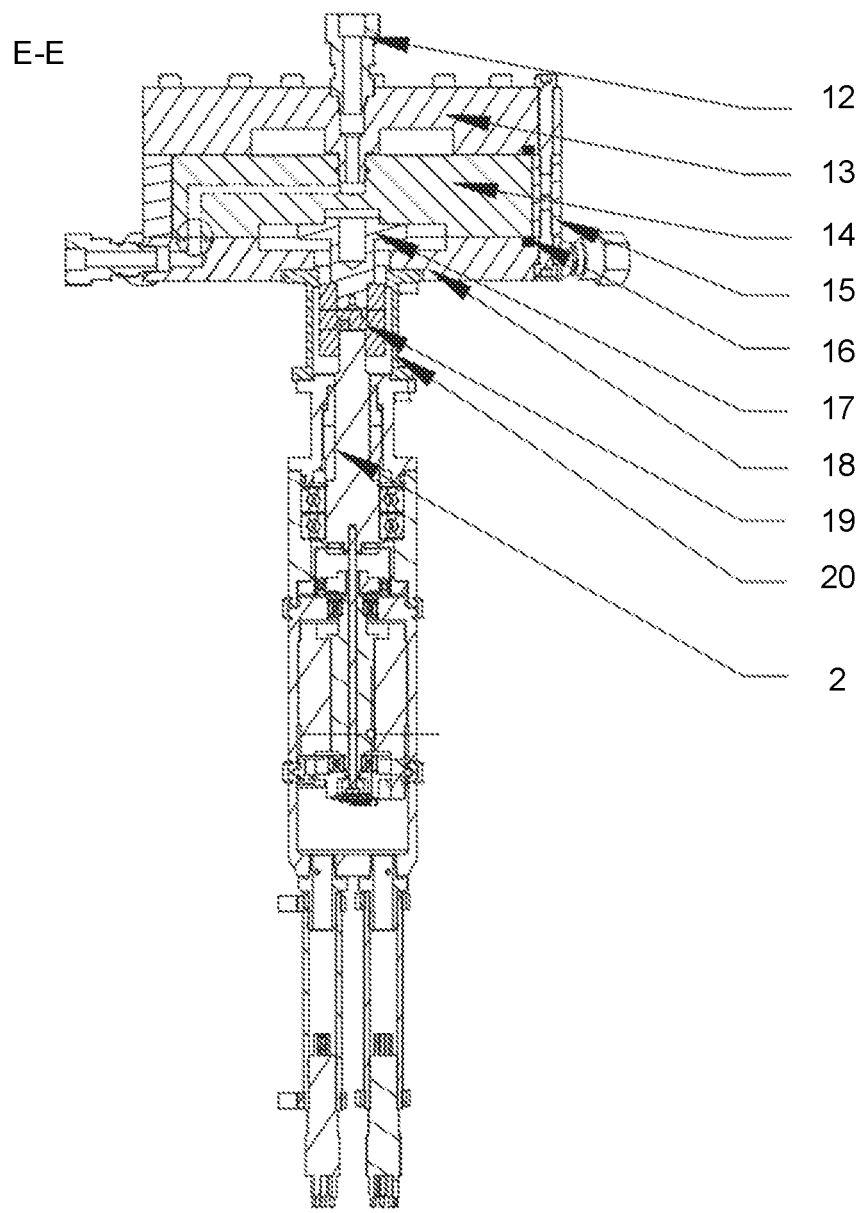
Figure 4:
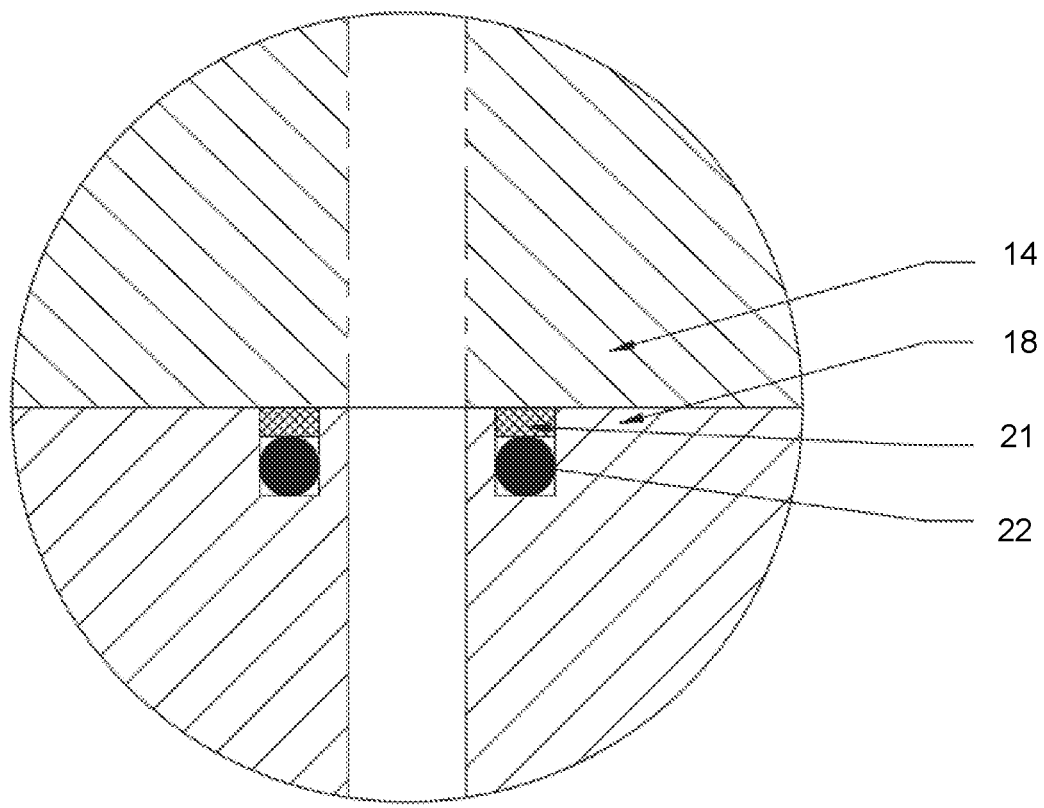
FIG. 4 is a schematic diagram illustrating a seal structure of a seawater flow channel inside a multi-channel circulation distributor of a large-flux in-situ filtration device for marine microorganism based on a multi-channel circulation distributor according to some embodiments of the present disclosure.

In some embodiments, the circulation distribution module may include the multi-channel circulation distributor 1, the deep-sea servo motor 2, etc. As shown in FIG. 3a, FIG. 3b, and FIG. 4, the multi-channel circulation distributor 1 and the deep-sea servo motor 2 may be connected through a coupling 19 and a shaft sleeve 20. The multi-channel circulation distributor 1 may specifically include: a plurality of pipe joints 12, an upper cover plate 13, a rotor 14, an outer shell 15, a spacer column 16, a transmission connection shaft 17, a lower cover plate 18, a coupling 19, a shaft sleeve 20, a polytetrafluoroethylene (PTFE) gasket 21, and an O-shaped rubber ring 22.

In some embodiments, the stainless steel gear pump 4 may be connected to the pipe joint 12 at a center of the upper cover plate 13. The lower cover plate 18 may include eight pipe joints 12 and an initial sealing position. The eight pipe joints and the initial sealing position may be evenly distributed on a side of the lower cover plate 18 in a circular array, and a difference between each two adjacent positions may be 40 degrees. The eight pipe joints 12 may be respectively connected to inlets of the filter film holders 3. An inside of the rotor may be provided with a unique water passage. One end of the water passage may be connected to a central water outlet of the upper cover plate 13, and other end of the water passage may be sequentially connected to eight water holes inside the lower cover plate 18 when the rotor rotates for one cycle.

In some embodiments, the upper cover plate 13, the outer shell 15, and the lower cover plate 18 may be fixed together to form a stator through screws. The rotor 14 may be located at an inner space of the stator. The rotor 14 may be fastened to the transmission connection shaft 17 through screws, and then connected to the deep-sea servo motor 2 through the coupling 19. The shaft sleeve 20 may be wrapped on an outside of the coupling 19 to fixedly connect the lower cover plate 18 and a shell body of the deep-sea servo motor 2. The deep-sea servo motor 2 may have the characteristics of large torque and low speed, and realize position control through encoder feedback, so as to complete precise flow channel switching and connection when driving the rotor 14 to rotate. In some embodiments, the deep-sea servo motor 2 may be a servo motor from Haoye Technology Co., Ltd., and the model of the servo motor may be: Z10-24-PBOF8M-6000-TI-CAN.

In some embodiments of the present disclosure, the multi-channel circulation distributor may be used, instead of using a large number of solenoid valves to switch flow channels, which may avoid the use of a large number of motor converters during the use of solenoid valves, and may also avoid possible faults caused by temperature rise due to long-term use of the solenoid valves. The single-channel connection and sealing of a plurality of filter membrane holes may be realized by the structural design of only one deep-sea servo motor and the multi-channel circulation distributor, thereby enhancing the stability of the device.

In some embodiments, the joint surface between the rotor 14 and the stator may be coated with new materials to enhance corrosion resistance and wear resistance, and reduce rotational friction. In the design and processing, the outer shell 15 surrounding the rotor may be 0.1-0.2 mm higher than the rotor 14, and a joint surface of the rotor 14 and the upper cover plate 13 or the lower cover plate 18 may be provided with a spacer column for keeping a space. The spacer column may be made of a PTFE material and distributed on the joint surface of the rotor 14 and the upper cover plate 13 or the lower cover plate 18, and the spacer column is 0.05-0.15 mm higher than the plane of the cover plates. The rotational friction may be reduced by the space between the rotor 12 and the stator, ensuring that the deep-sea servo motor 2 may drive the rotor 14 normally.

As shown in FIG. 4, in some embodiments, in the multi-channel circulation distributor 1, a seawater channel at a joint surface between the rotor 14 and the lower cover plate 18 may be sealed with an O-shaped PTFE gasket 21 and an O-shaped rubber ring 22, the O-shaped rubber ring 22 may be located at a bottom of a groove and used for compensating a space at the joint surface using self-elasticity of the O-shaped rubber ring to reduce a seawater leakage; and the PTFE gasket 21 may be placed above the O-shaped rubber ring and close to a surface of the rotor for realizing sliding sealing using self-lubrication of PTFE gasket.

Figure 5A:
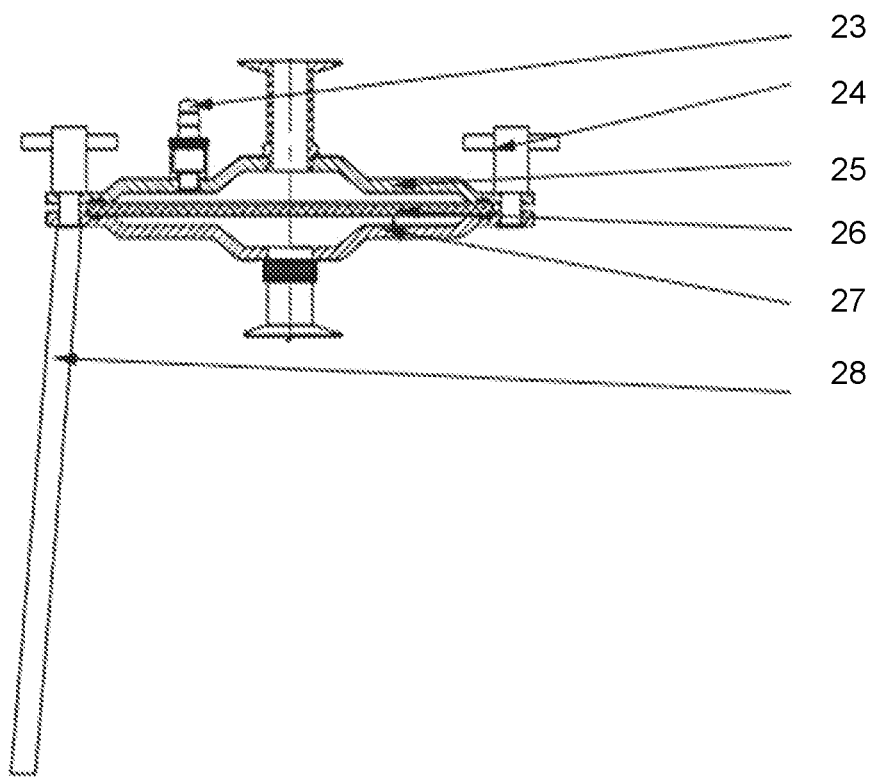
FIG. 5a and FIG. 5b are schematic diagrams illustrating sectional structures of filter film holders of a large-flux in-situ filtration device for marine microorganism based on a multi-channel circulation distributor according to some embodiments of the present disclosure.
Figure 5B:
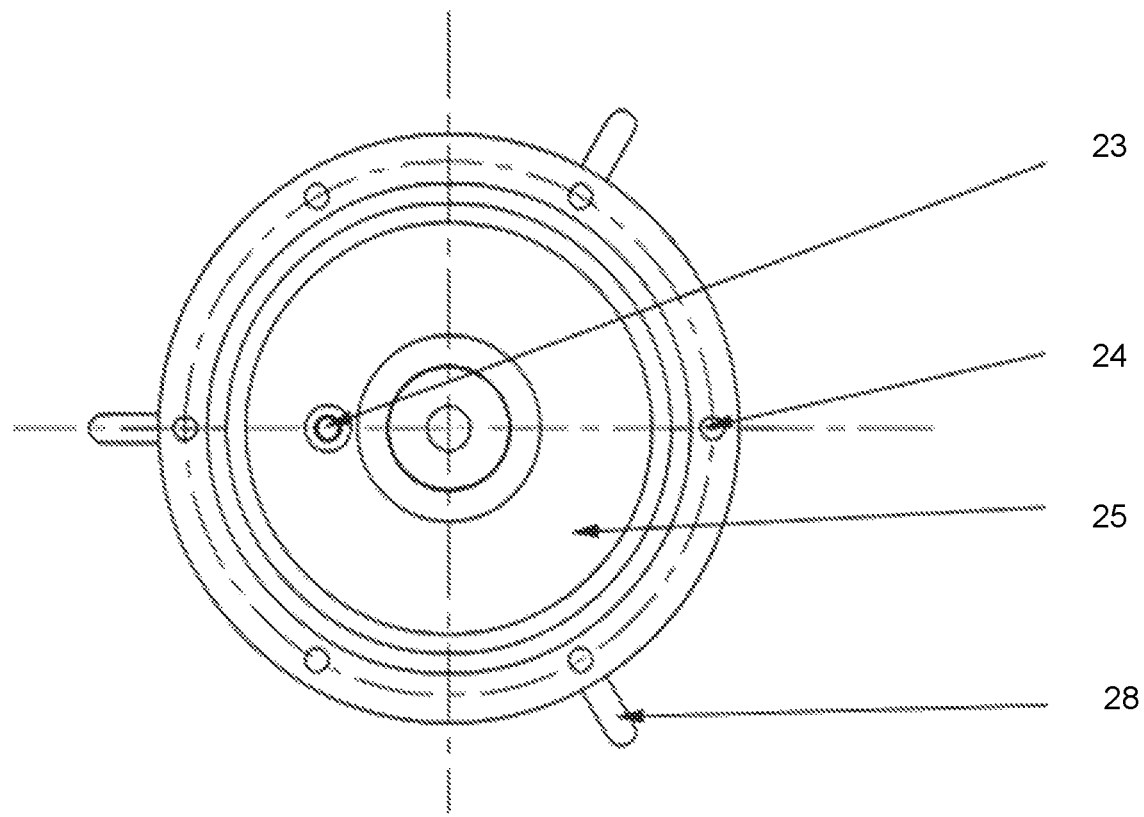

In some embodiments, the filtration module may include eight filter film holders 3. All the filter film holders 3 may be distributed around the multi-channel circulation distributor in a circular array. As shown in FIG. 5a and FIG. 5b, the filter film holders 3 may all be stainless steel disc single-layer flat filters, each of which may include an exhaust valve 23, set screws 24, an upper cover plate 25, a support mesh plate 26, a lower cover plate 27, and a bracket 28. During use, the upper cover plate 25 and the lower cover plate 27 may be fixed through four-eight set screws 24 and the support mesh plate 26 in the middle may be clamped. Filter films with a diameter of 142 mm and an aperture of 0.22 μm may be placed on the support mesh plate 26 as pressure support surfaces of microporous films, to ensure that the filter films may not be liable to break under the filtration pressure.

In some embodiments, before filtration, the air inside the filter film holders 3 may be discharged through the exhaust valves 23, then the seawater may flow in from the joint at the centers of the upper cover plates 25, and pass through the filter films laid on the support mesh plate 26 and flow out of the filter film holders 3 from the joint at the centers of the lower cover plates 27, in this process, the microorganism in the seawater may be enriched on the filter films. In some embodiments, the bracket 28 of the filter film holders 3 may be removed and the filter film holders 3 may fixed on the main body support frame 11 by buckles. In some embodiments, more filter film holders 3 may be arranged to increase the filtration flux. For example, the number of pipe joints 12 connected to the lower cover plate 18 may be increased by reducing an angle between the adjacent pipe joints 12 on a side of the lower cover plate 18 of the multi-channel circulation distributor 1, thereby connecting more filter film holders.

In some embodiments, the pump module may include a stainless steel gear pump 4, a deep-sea drive motor 5, or the like. Similar to the connection mode of the circulation distributor module, the stainless steel gear pump 4 and the deep-sea drive motor 5 may be connected through a coupling. An outer side of the coupling may be fixed with a shaft sleeve. The deep-sea drive motor 5 may adopt speed loop and power loop control, and the speed of the deep-sea drive motor 5 may be adjustable.

In some embodiments of the present disclosure, after the deployment of the large-flux in-situ filtration device for the marine microorganism based on the multi-channel circulation distributor is completed, a large amount of seawater may be injected into the filter film holders through the pressure generated by the gear pump to complete microbial enrichment and filtration. After completing a set of filtration processes, the energy and control module may drive the multi-channel circulation distributor to switch the seawater flow channel inside the device to connect to the unused filter film holders to perform filtration again, so as to obtain a plurality of sets of filtered samples and avoid blockage of the filter films caused by filtration of a large amount of seawater.

Compared with the prior art, a plurality of sets of marine microbial filtration samples may be obtained by one deployment. Compared with the conventional seawater microbial collection that only one filter film is used for enrichment and filtration, the obtained biomass may be increased several times. A large amount of microbial samples may be quickly obtained within a short time period, providing sufficient samples for subsequent genomics analysis.

In some embodiments, the filtration volume measurement module may include a water meter 8, a camera 9, and an LED light 10. The water meter 8 may be connected to an outlet of the stainless steel gear pump 4 to measure a volume of filtered seawater, and display the volume of filtered seawater on a dial. When the LED light 10 provides a light source, the camera may automatically photograph and record data of the volume of filtered seawater corresponding to each set of samples.

In some embodiments, the device may further include two pressure sensors, which may be respectively installed at an inlet and an outlet of the multi-channel circulation distributor 1. The two pressure sensors may be configured to detect a pressure at both ends of the multi-channel circulation distributor 1. The energy and control module may control a driving force of the stainless steel gear pump 4 through the pressure.

In some embodiments, the device may further include a primary filter, which may be installed at an inlet of the device to prevent damage or blockage of the filter films caused by inhalation of small organisms and large particles into the device.

In some embodiments, the device may further include a temperature-salt-depth sensor, which may be fixed on the main body support frame 11 and connected to the energy and control module using a watertight cable to obtain basic background data of an in-situ sampling.

In some embodiments, the device may further include an underwater acoustic communicator, which may be fixed on the main body support frame 11 and connected to the energy and control module using a watertight cable. The underwater acoustic communicator may realize data transmission and real-time instruction issuance between the device and a host computer during a sampling process.

The working process of the large-flux in-situ filtration device for the marine microorganism based on the multi-channel circulation distributor may have the following operations.

The in-situ filtration device may be deployed by a winch. Before the device enters the seawater, the host computer may send task parameters to set a start time or filter according to pressure depth feedback. After the device reaches a predetermined depth (or time), the energy and control module may control the deep-sea servo motor 2 to drive the rotor 14 of the multi-channel circulation distributor 1 to connect the target filter film holder 3, and then control the deep-sea drive motor 5 to drive the gear pump 3 to run to inject the seawater into the multi-channel circulation distributor 1, thereby making the seawater continue to flow through the multi-channel circulation distribution 1 to enter the filter film holder 3 to realize in-situ enrichment and filtration. The filtered seawater may flow out of the device through the water meter 4.

In some embodiments, after a set of samples are filtered, the energy and control module may control the LED light 8 to turn on, use the camera 10 to photograph the filtered water volume, and then send an instruction according to the task parameters sent by the host computer before entering the water, to control the deep sea servo motor 2 to drive the rotor 14 to rotate to the preset seawater flow channel corresponding to the unused filter film holder 3 for the next set of filtration. Then the above operations may be repeated until the filtration is completely completed.

In some embodiments, after the filtration is completed, the energy and control module may send an instruction to shut down the deep-water motor, and wait for being recovered. After being recovered, a plurality of sets of in-situ filtered microbial samples may be obtained by only taking out the filter films in the filter film holders 3 (i.e., one deployment) for subsequent genomics research. The volume of seawater samples filtered by each filter film holder may be recorded by the filtration volume measurement module.

In some embodiments of the present disclosure, the entire set of device may operate independently and autonomously under water. The in-situ enrichment and filtration may avoid the pollution of the extraction process of the shipboard laboratory (deck), and the automatic operation may greatly reduce the workload of deck filtration for scientific expedition personnel.

In some embodiments, an outside of the filter film holders may be provided with a shell body. A piston end cover may be fitted on the shell body, and the end cover may be connected to a hydraulic rod of a hydraulic device inside the shell body. The hydraulic rod may be configured to control a position of the end cover in the shell body to apply pressure to a liquid environment inside the shell body through the end cover.

The shell body refers to a device used to enclose a test environment for in-situ enrichment and culture of deep-sea microorganism. The shell body may be made of various materials, and the shell body may be various shapes. For example, the material of the shell body may be iron, copper, steel, or the like. As another example, the shape of the shell body may be a cylinder, a cube, or the like. The material and the shape of the shell body may not be limited here.

The piston end cover refers to a device used to apply pressure to the inside of shell body. In some embodiments, the end cover may be a pair of devices respectively located at upper and lower ends of the shell body. The pressure of the liquid environment inside the shell body may be controlled by moving the end cover in the shell body. The end cover may be made of various materials, and the shape of the end cover may be adapted to a shape of an inner cavity of the shell body. For example, the material of the piston end cover may be iron, copper, steel, or the like.

The hydraulic device refers to a device used to drive the piston end cover to apply pressure to the inside of the shell body. In some embodiments, the hydraulic unit may have a plurality of hydraulic rods connected to the piston end cover. The hydraulic device may drive the piston end cover to move in the shell body by stretching the hydraulic rod, and then adjust the pressure inside the shell body. For example, when pressure is increased inside the shell body, the hydraulic device may control the hydraulic rod to extend to drive the piston end cover to move in the shell body. Then the piston end cover may squeeze the inside of the shell body to increase the pressure inside the shell body.

In some embodiments, an inner wall of the shell body may be provided with an internal temperature-salt-depth sensor. The internal temperature-salt-depth sensor may be configured to monitor at least one of an internal temperature, an internal pressure, and electrical conductivity information of the shell body. Detection data of the internal temperature-salt-depth sensor may be regularly transmitted back to the host computer through the underwater acoustic communicator for storage.

The internal temperature-salt-depth sensor refers to a device configured to monitor at least one of an internal temperature, an internal pressure, and electrical conductivity information of the shell body. For example, the internal temperature-salt-depth sensor may be an optic fiber marine temperature-salt-depth sensor. The internal temperature of the shell body refers to a temperature of an environment inside the shell body where the microorganism is located. The internal pressure of the shell body refers to a pressure of the environment inside the shell body where the microorganism is located. The electrical conductivity information refers to water body conductivity (e.g., salinity) of the environment inside the shell body where the microorganism is located.

In some embodiments, the detection data of the internal temperature-salt-depth sensor may be regularly transmitted back to the host computer through the underwater acoustic communication device for storage. For more descriptions of the internal temperature-salt-depth sensor, the underwater acoustic communicator, and the host computer, please refer to FIGS. 1-5b and the related descriptions thereof.

In some embodiments, a temperature adjustment device may be arranged outside the shell body. The temperature adjustment device may include a copper pipe arranged around the shell body. The temperature adjustment device may be configured to adjust the internal temperature of the shell body.

The temperature adjustment device refers to a device for adjusting the internal temperature of the shell body. The temperature adjustment device may include a copper pipe and a power device, and the copper pipe and the power device may correspond to different temperature adjustment modes. For example, the power device in the temperature adjustment device may be a compression refrigerator, an absorption refrigerator, a heat pump, or the like.

In some embodiments, the copper pipe may be wrapped around the shell body. When the external seawater flowing into the copper pipe flows around the shell body, the seawater may flush the shell body, thereby cooling or heating the shell body. When the copper pipe is emptied of seawater and sealed, the copper pipe may make the shell body in a sealed environment, which may play a role of heat preservation to a certain extent.

Figure 8:
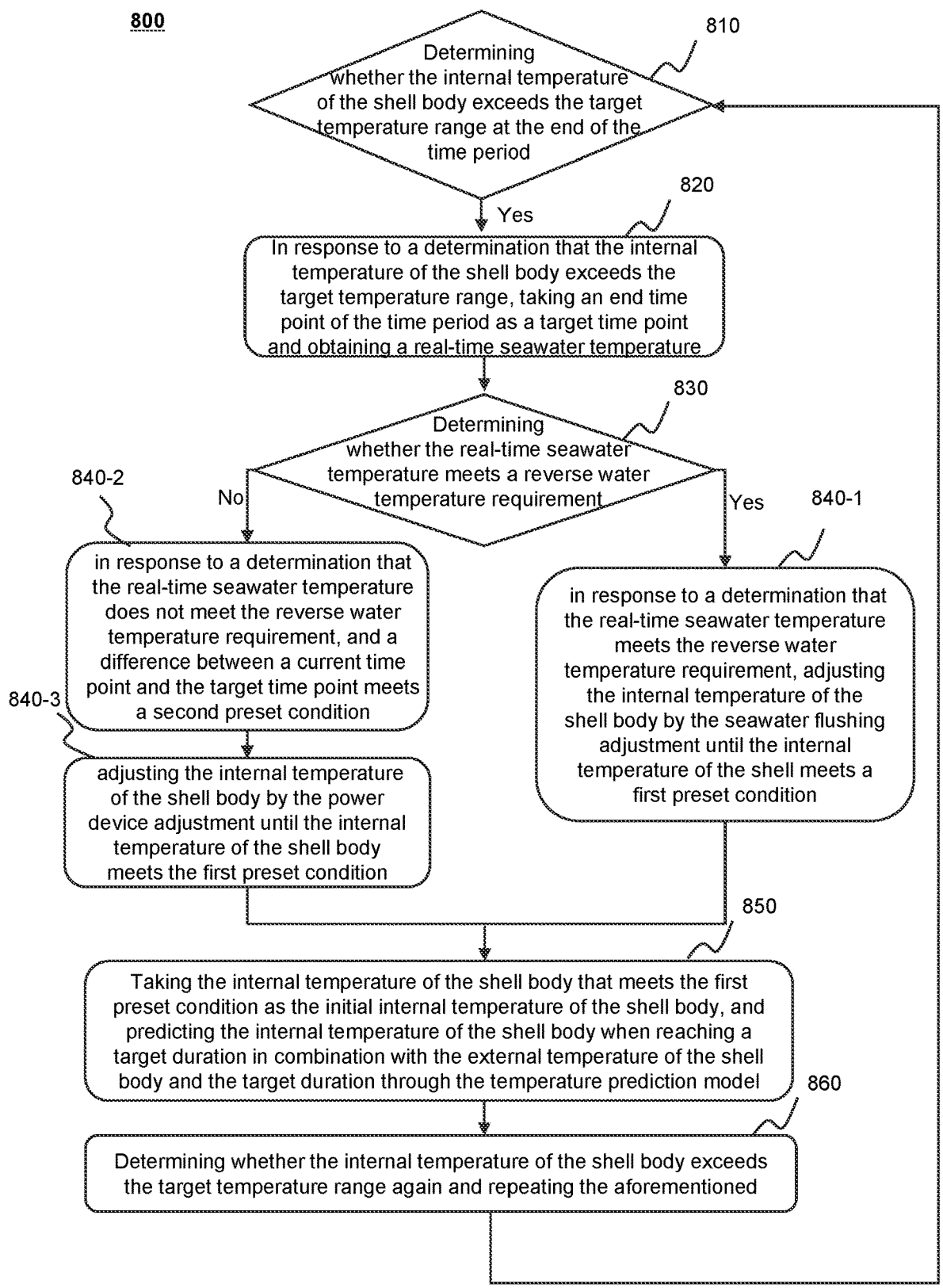
FIG. 8 is a flowchart illustrating an exemplary process of adjusting an internal temperature of a shell body according to some embodiments of the present disclosure.

For more descriptions of temperature adjustment, please refer to the following and related descriptions in FIG. 8.

In some embodiments, the power and control module may be further configured to control the hydraulic device in the shell body to apply the pressure to the end cover.

For example, the energy and control module may be further configured to control the pressure applied by the hydraulic device on the end cover by controlling the hydraulic device in the shell body and keep a stability of the internal pressure of the shell body by locking the hydraulic rod or the end cover.

In some embodiments, the stability of the environment where the collected deep-sea microbial samples are located may be kept by controlling the pressure and the temperature of the liquid environment inside the shell body, thereby making the internal temperature and pressure of the shell body meet the requirements for keeping the activity of the deep-sea microbial samples.

In some embodiments, the energy and control module may be further configured to control the pressure applied by the hydraulic device on the end cover based on the internal pressure of the shell body and a seawater pressure to keep a stability of the internal pressure of the shell body. The seawater pressure refers to a pressure of seawater at a water depth where the in-situ filtration device is located. In some embodiments, if the internal pressure of the shell body needs to be consistent with the seawater pressure, the pressure applied by the hydraulic device on the end cover may be determined according to a difference between the seawater pressure and the internal pressure of the shell body. For example, if the seawater pressure is greater than the internal pressure of the shell body, the pressure applied by the hydraulic device on the end cover may be the difference between the seawater pressure and the internal pressure of the shell body.

In some embodiments, the internal pressure of the shell body may be monitored by the internal temperature-salt-depth sensor. The seawater pressure may be determined based on the seawater depth of a position where the in-situ filtration device collects the microorganism. For example, the seawater pressure may be determined by retrieving the water depth from a database. The database may be created based on the seawater pressure corresponding to historical seawater depths.

In some embodiments, the internal pressure of the shell body may be stabilized within a range where the deep-sea microorganism keeps active, so the determined seawater pressure may be used as the pressure at which the deep-sea microorganism keeps active. Therefore, the pressure applied by the hydraulic device on the end cover may be controlled, and when the internal pressure of the shell body reaches the requirement, the internal pressure of the shell body may be kept stable at the seawater pressure by locking the hydraulic rod or the end cover. For example, the internal pressure of the shell body may be monitored as 10.05 MPa by the internal temperature-salt-depth sensor, the seawater pressure may be retrieved to be 10.06 Mpa, and then the internal pressure of the shell body may be stabilized at 10.06 Mpa by applying pressure on the end cover by the hydraulic device.

In some embodiments, the temperature adjustment device may be further configured to adjust the internal temperature of the shell body based on the internal temperature of the shell body and the seawater temperature to keep the stability of the internal temperature of the shell body. The seawater temperature refers to a temperature of seawater in a sea area and at a water depth of a position where the in-situ filtration device is located.

In some embodiments, the internal temperature of the shell body may be monitored by the internal temperature-salt-depth sensors. The seawater temperature may be obtained by a temperature sensor arranged on the in-situ filtration device.

In some embodiments, the internal temperature of the shell body may be stable within a range where the deep-sea microorganism keeps active, so the obtained seawater temperature may be used as the temperature at which the deep-sea microorganism keeps active. Therefore, the temperature adjustment device may keep the internal temperature of the shell body stable at the seawater temperature by adjusting the internal temperature of the shell body. For example, if the internal temperature of the shell body is monitored as 5.0° C. by the internal temperature-salt-depth sensor, and the seawater temperature is monitored as 4.5° C. by the temperature sensor, then the temperature adjustment device may stabilize the internal temperature of the shell body at 4.5° C. by adjusting the internal temperature of the shell body. For example, if the internal temperature of the shell body is 5.0° C., the external seawater with a temperature of 4.5° C. may be piped into the copper pipe wrapped around the shell body, and the seawater may flush the shell body and cool down the internal temperature of the shell body through heat transfer.

In some embodiments, components with computing functions such as a chip and a control module may be set in the temperature adjustment device, so that the temperature adjustment device may predict the internal temperature of the shell body based on the obtained data and determine a corresponding temperature adjustment time node, and adjust the internal temperature of the shell body at the corresponding temperature adjustment time node, thereby keeping the internal temperature of the shell body stable within the target temperature range. For more descriptions, please refer to the related descriptions in FIG. 6.

In some embodiments of the present disclosure, the internal pressure and temperature of the shell body may be adjusted by corresponding devices, so that the internal temperature and pressure of the shell body may be stable to keep the deep-sea microorganism active, ensuring that the amount of microorganism is sufficient to use for researchers.

Figure 6:
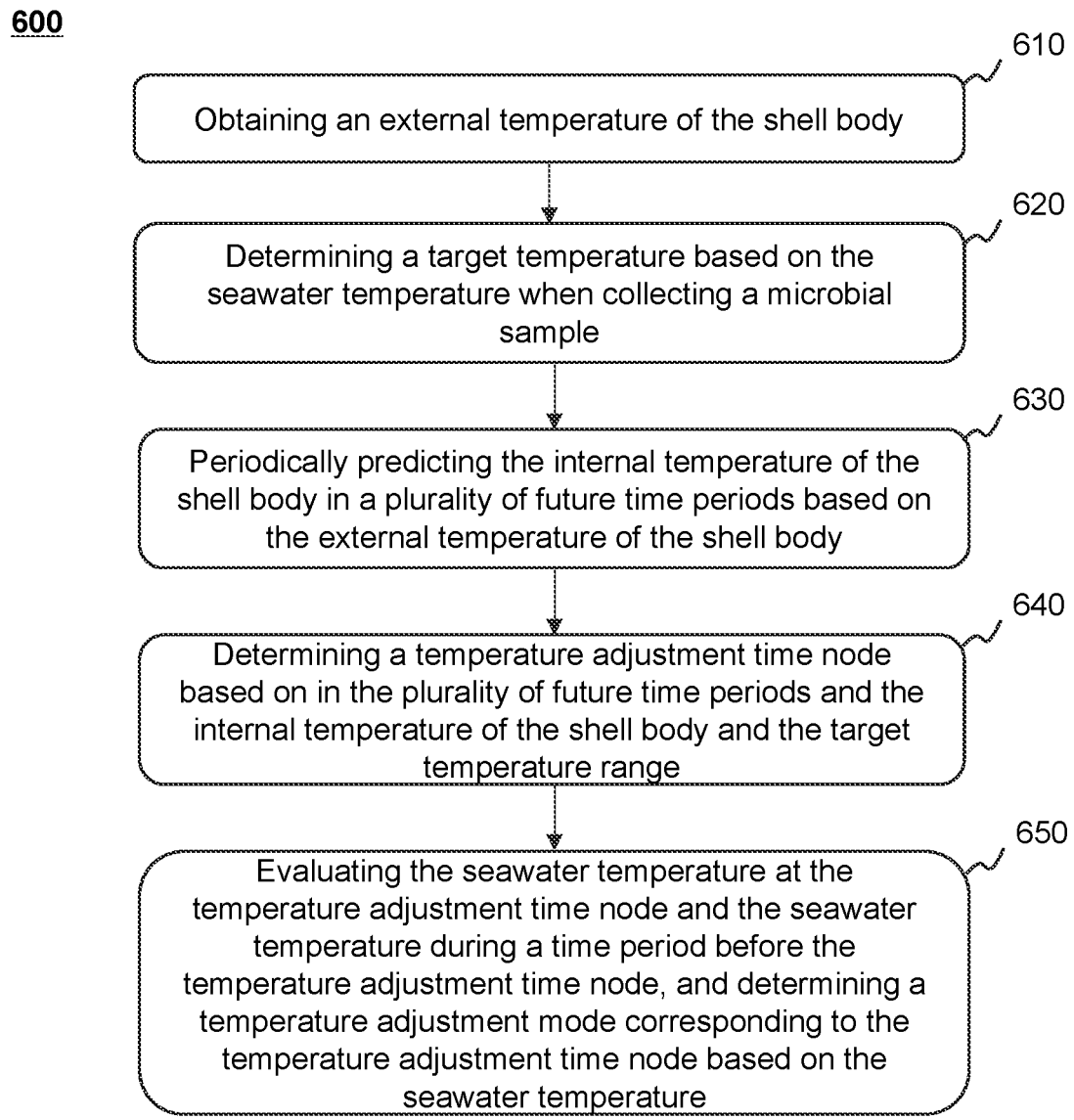
FIG. 6 is flowchart illustrating an exemplary process of determining a temperature adjustment mode according to some embodiments of the present disclosure.

FIG. 6 is a flowchart illustrating an exemplary process of determining a temperature adjustment mode according to some embodiments of the present disclosure. As shown in FIG. 6, the process 600 may include the following operations. In some embodiments, the process 600 may be performed by a temperature adjustment device.

In 610, an external temperature of the shell body may be obtained.

The external temperature of the shell body refers to a temperature at a position between the shell body and the in-situ filtration device. The external temperature of the shell body may be obtained by the temperature sensor and transmitted to the temperature adjustment device.

In some embodiments, there may be a certain difference among the external temperature of the shell body, the internal temperature of the shell body, and the seawater temperature due to heat transfer such as heat generated by the corresponding components inside and outside the shell body during working.

In 620: a target temperature range may be determined based on the seawater temperature when collecting a microbial sample.

In some embodiments, the target temperature range may be a temperature range capable of keeping the deep-sea microorganism active. For example, the target temperature range refers to a seawater temperature range monitored when collecting the microbial samples by each filter film holder. The temperature adjustment device may obtain the seawater temperature when the filter film holders collect the microbial samples through the temperature sensor, and determine the obtained seawater temperature as the target temperature range.

In 630, the internal temperature of the shell body in a plurality of future time periods may be periodically predicted based on the external temperature of the shell body.

The internal temperature of the shell body refers to a temperature of the environment inside the shell body where the microorganism may be located at a corresponding time point.

In some embodiments, the plurality of future time periods may include a plurality of time periods in the future. A duration range of each time period may be preset. For example, the plurality of future time periods may be respectively a time period 1 corresponding to 1 hour to 2 hours in the future, a time period 2 corresponding to 2 hours to 3 hours in the future, etc. As another example, if the current time is 8:00, then the plurality of future time periods may be a time period 1 from 8:00 to 8:30 and a time period 2 from 8:30 to 9:00, etc.

In some embodiments, the temperature adjustment device may periodically predict the internal temperature of the shell body in the plurality of future time periods based on the external temperature of the shell body. For example, the temperature adjustment device may predict the internal temperature of the shell body corresponding to an end point of a time period 1 based on the current external temperature of the shell body, and then predict the internal temperature of the shell body corresponding to an end point of a time period 2 according to the current external temperature of the shell body at the end point of the time period 1. The operations may be repeated accordingly, to periodically predict the internal temperature of the shell body in the plurality of future time periods.

It should be noted that the temperature adjustment device may also predict the internal temperature of the shell body after any time period at any intermediate time point in any time period based on the external temperature of the shell body at this time point.

In some embodiments, the temperature adjustment device predicting the internal temperature of the shell body after a certain time period based on the external temperature of the shell body at a certain time point may be implemented based on vector retrieval. For example, the temperature adjust device may construct a vector p(a, b, c) to be matched based on the external temperature of the shell body, the internal temperature of the shell body, and a duration to be predicted corresponding to this time point, where a represents the external temperature of the shell body corresponding to the time point, b represents the internal temperature of the shell body corresponding to the time point, and c represents the duration to be predicted.

The temperature adjustment device may obtain a reference vector by retrieving the constructed vector to be matched in a vector database. A number of historical vectors may be stored in the vector database. The historical vectors may be constructed based on historical data obtained in the same sea area. Each historical vector may represent the external temperature of the shell body, the internal temperature of the shell body, and the duration to be predicted at the corresponding historical time. In the vector database, each historical vector may also be associated and stored with an actual internal temperature of the shell body after the corresponding duration to be predicted.

In some embodiments, the temperature adjustment device may use the historical vector with the smallest vector distance from the vector to be matched as the reference vector, and use the actual internal temperature of the shell body after the duration to be predicted corresponding to the reference vector as the predicted internal temperature of the shell body.

In some embodiments, the internal temperature of the shell body in the plurality of future time periods may also be obtained based on a machine learning model, such as a temperature prediction model.

Figure 7:
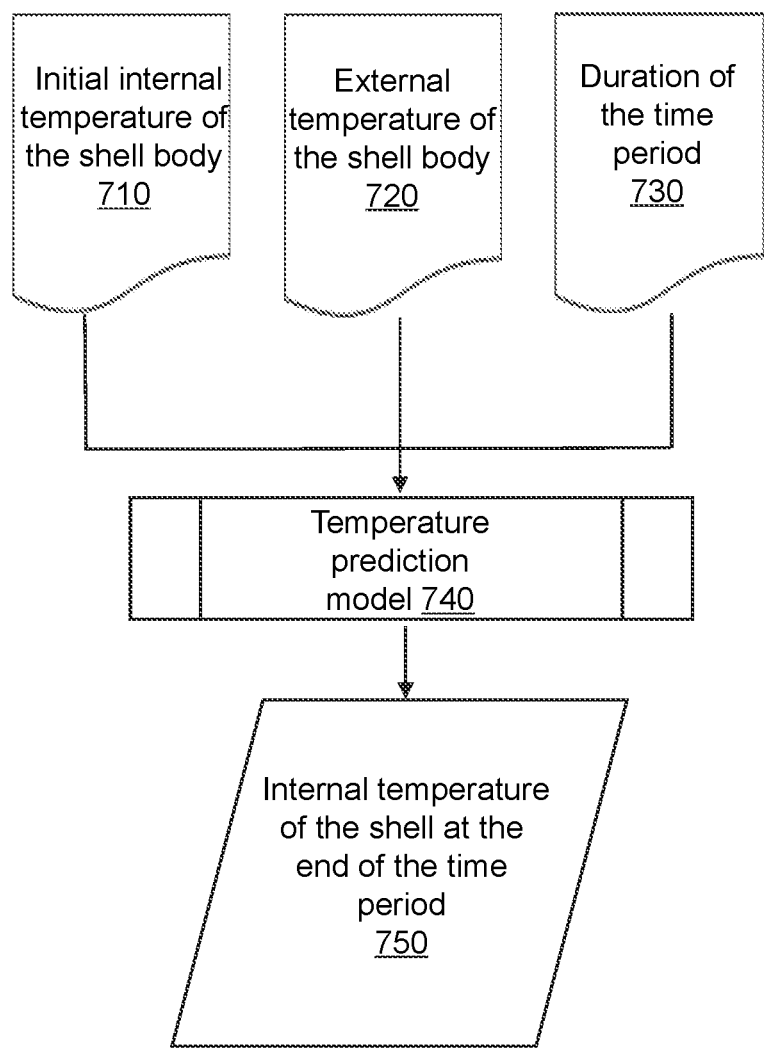
FIG. 7 is schematic diagram illustrating an exemplary temperature prediction model according to some embodiments of the present disclosure.

FIG. 7 is a schematic diagram illustrating a temperature prediction model according to some embodiments of the present disclosure.

In some embodiments, the temperature adjustment device may be further configured to, for each of the plurality of future time periods, predict the internal temperature 750 of the shell body when the time period ends through a temperature prediction model based on an initial internal temperature 710 of the shell body in the time period, the external temperature 720 of the shell body, and a duration 730 of the time period, and the temperature prediction model may be a machine learning model.

In some embodiments, an input of the temperature prediction model 740 may include the initial internal temperature 710 of the shell body, the external temperature 720 of the shell body, and the duration 730 of the time period. The initial internal temperature 710 of the shell body refers to a temperature of the environment inside the shell body where the microorganism is located at the beginning of each of the plurality of future time periods. The external temperature 720 of the shell body refers to a temperature at a position between the shell body and the in-situ filtration device at the beginning of each of the plurality of future time periods. The duration 730 of the time period refers to a duration of each time period of the plurality of future time periods. An output of the temperature prediction model may include the internal temperature 750 of the shell body at the end of the time period.

In some embodiments, the initial internal temperature of the shell body at the beginning of each time period, the external temperature of the shell body, and the duration of the time period may be obtained respectively. The internal temperature of the shell body at the end of each time period may be predicted through the temperature prediction model, so as to predict the internal temperature of the shell body of the plurality of future time periods.

In some embodiments, training sample data of the temperature prediction model may include sample internal temperature of the shell body, sample external temperature of the shell body, and a duration of a sample time period monitored in the historical data. Labels may be the actual internal temperature of the shell body at the end of the sample time period after the internal temperature of the shell monitored in the historical data passes the duration of the sample time period.

During training, the internal temperature of the shell body at the end of the time period may be output by the temperature prediction model by inputting the sample internal temperature of the shell body, the sample external temperature of the shell body, and the duration of the sample time period into the temperature prediction model. During the training process, the temperature adjustment device may construct a loss function based on the internal temperature of the shell body in the labels and the internal temperature of the shell body output by the temperature prediction model. Besides, parameters of the temperature prediction model may be updated until a preset condition is satisfied, and the training may be completed. The preset condition may be one or more of the loss function being less than a threshold, converging, or the training period reaching a threshold, or the like.

In some embodiments of the present disclosure, the internal temperature of the shell body may be predicted using the trained temperature prediction model to effectively obtain the internal temperature of the shell in the future time period, thereby using an accurate temperature adjustment mode.

In 640, a temperature adjustment time node may be determined based on the internal temperature of the shell body in the plurality of future time periods and the target temperature range.

The temperature adjustment time node refers to a time point when the temperature inside the shell body needs to be adjusted. In some embodiments, the temperature adjustment device may determine the temperature adjustment time node based on the predicted internal temperature of the shell body in the plurality of future time periods and the target temperature range. For example, when the predicted internal temperature of the shell body at a time point corresponding to a certain time period does not belong to the target temperature range, the time point may be determined as the temperature adjustment time node.

In 650, the seawater temperature at the temperature adjustment time node and the seawater temperature during a time period before the temperature adjustment time node may be evaluated, and a temperature adjustment mode corresponding to the temperature adjustment time node may be determined based on the seawater temperature.

The temperature adjustment mode refers to a mode capable of adjusting the internal temperature of the shell body. The temperature adjustment mode may include at least one of a seawater flushing adjustment and a power device adjustment.

In some embodiments, the mode of the seawater flushing adjustment may be that the flowing external seawater may be piped through the copper pipe wrapped around the shell body, and when the seawater in the copper pipe flows around the shell body, the seawater may flush the shell body to cool or heat up the shell body.

In some embodiments, the mode of the power device adjustment may be that a power device may be started to work through power storage, thereby adjusting the internal temperature of the shell body. For example, the internal temperature of the shell body may be raised by activating a heat pump using the power storage. As another example, a power source may collect and store heat energy released inside the shell body through the heat dissipation copper pipe, and then drive devices such as a compression refrigerator to cool down the inside of the shell body using the power storage.

Evaluating the seawater temperature refers to predicting the seawater temperature corresponding to the corresponding time node. In some embodiments, the temperature adjustment device may obtain changes of the seawater temperature in historical time periods based on the currently monitored seawater temperature information in the historical time periods, thereby estimating the seawater temperature in a future time period based on the changes of the seawater temperature in the historical time periods.

Merely by way of example, the current time may be 8:00, the temperature adjustment time node may be 9:00, the current seawater temperature at the current position may be 5° C., the seawater temperature at the current position at 6:00 may be 3° C., the seawater temperature at 6:30 may be 4° C., the seawater temperature at 7:00 may be 4.6° C., and the seawater temperature at 7:30 may be 4.8° C. It can be seen that a rise rate of the seawater temperature may get more slowly, and the seawater temperature may be more likely to rise less than 0.5 degrees in the next hour. It may be predicted that the seawater temperature at 8:30 may be within a range of 5° C.-5.3° C., and the seawater temperature at 9:00 may be within a range of 5° C.-5.5° C.

In some embodiments, the temperature adjustment device may determine the temperature adjustment mode for adjusting the internal temperature of the shell body based on the obtained seawater temperature at the temperature adjustment time node. For example, if the predicted internal temperature of the shell body at the temperature adjustment time node is higher than the target temperature range, and there is a time period in which the seawater temperature is lower than the internal temperature of the shell body within a time period before the temperature adjustment time node, the internal temperature of the shell body may be adjusted using the mode of the seawater flushing adjustment during this time period. As another example, if the predicted internal temperature of the shell body at the temperature adjustment time node is lower than the target temperature range, and there is no time period in which the seawater temperature is higher than the internal temperature of the shell body at the temperature adjustment time node and within a time period before the temperature adjustment time node, the internal temperature of the shell body may be adjusted using the mode of the power device adjustment at an appropriate time period in advance based on the temperature adjustment time node.

In some embodiments, the temperature adjustment device may determine the corresponding adjustment mode based on whether the seawater temperature meets a reverse water temperature requirement. For details, please refer to related description of FIG. 8.

In some embodiments of the present disclosure, the seawater temperature obtained when collecting the microorganism may be used as the target temperature range, different temperature adjustment modes may be determined for the inside of the shell body at the determined temperature adjustment time node, and different temperature adjustment modes may be more flexibly and effectively adjust the internal temperature of the shell body to stabilize within the target temperature range, thereby ensuring that the deep-sea microorganism may be within the temperature range that keeps the activity. In addition, the temperature adjustment mode may first use the external seawater to flush the shell body, and use the seawater temperature to adjust the internal temperature of the shell body, which may effectively adjust the temperature and save energy consumption of the device.

FIG. 8 is flowchart of an exemplary process of adjusting internal temperature of a shell body according to some embodiments of the present disclosure. As shown in FIG. 8, the process 800 may include the following operations. In some embodiments, the process 800 may be performed by a temperature adjustment device.

In 810, it may be determined whether the internal temperature of the shell body exceeds the target temperature range at the end of the time period.

For more descriptions of the target temperature range and the internal temperature of the shell body, please refer to FIG. 6 and related contents thereof.

In 820, in response to a determination that the internal temperature of the shell body exceeds the target temperature range, an end time point of the time period may be taken as a target time point and a real-time seawater temperature may be obtained.

In some embodiments, if the internal temperature of the shell body exceeds the target temperature range, it may indicate that the corresponding internal temperature of the shell body at the end point of the corresponding time period may not meet the temperature requirement for the microorganism to keep active.

The target time point refers to a time point at which the internal temperature of the shell body is adjusted. In some embodiments, if the internal temperature of the shell body at a certain time point exceeds the target temperature range, this time point may be taken as the target time point.

The real-time seawater temperature refers to a temperature of seawater obtained in real time. In some embodiments, the temperature adjustment device may obtain the real-time seawater temperature by monitoring the seawater in real time through the temperature sensor.

In 830, it may be determined whether the real-time seawater temperature meets a reverse water temperature requirement.

The reverse water temperature refers to seawater temperature that meets the seawater flushing adjustment. The reverse water temperature requirement represents that the seawater temperature needs to meet the requirements of the temperature range of the reverse water temperature. In some embodiments, the reverse water temperature may be related to the predicted internal temperature of the shell body and the target temperature range. For example, if the predicted internal temperature of the shell body is greater than a maximum temperature of the target temperature range, the reverse water temperature may include a water temperature that is less than or equal to the maximum temperature of the target temperature range. As another example, if the predicted internal temperature of the shell body is lower than a minimum temperature of the target temperature range, the reverse water temperature may be a water temperature that is greater than or equal to the minimum temperature of the target temperature range. For example, if the predicted internal temperature of the shell body at 15:00 is 8° C., which is higher than the maximum temperature of 5° C. of the target temperature range of 3-5° C., the reverse water temperature may be the water temperature less than or equal to 5° C., i.e., the reverse water temperature requirement may be that the real-time seawater temperature may be less than or equal to 5° C.

In 840, in response to a determination that the real-time seawater temperature meets the reverse water temperature requirement, the internal temperature of the shell body may be adjusted by the seawater flushing adjustment until the internal temperature of the shell meets a first preset condition.

In some embodiments, adjusting the internal temperature of the shell body using the seawater flushing adjustment may be to pipe seawater that meets the reverse water temperature requirement into the copper pipe, making the seawater flow around the shell body and flush the shell body to adjust the internal temperature of the shell body through heat transfer. For example, it is predicted that the internal temperature of the shell body at 15:00 may be 8° C., and the target temperature range may be 3-5° C.; the seawater temperature may be 4° C. at 14:40, which meets the reverse water temperature requirement, then the seawater may be piped into the copper pipe at 14:40, and the internal temperature of the shell body may be adjusted by the seawater flushing adjustment.

The first preset condition may be that the adjusted internal temperature of the shell body may be within the target temperature range, and a difference between the adjusted internal temperature of the shell body and the maximum or minimum temperature of the target temperature range may be less than or equal to a preset distance threshold. The preset distance threshold may be determined based on the historical data, such as 1° C., 0° C., or the like.

In some embodiments, if the predicted internal temperature of the shell body is greater than the maximum temperature of the target temperature range at the end of the time period, the first preset condition at this time may be that the adjusted internal temperature of the shell body is within the target temperature range, and the difference between the adjusted internal temperature of the shell body and the minimum temperature of the target temperature range may be less than or equal to the preset distance threshold.

In some embodiments, if the predicted internal temperature of the shell body is less than the minimum temperature of the target temperature range at the end of the time period, the first preset condition at this time may be that the adjusted internal temperature of the shell body is within the target temperature range, and the difference between the adjusted internal temperature of the shell body and the maximum temperature of the target temperature range may be less than or equal to the preset distance threshold.

In some embodiments, when the real-time seawater temperature meets the reverse water temperature requirement, the internal temperature of the shell body may be adjusted using the seawater flushing adjustment until the internal temperature of the shell body meets the first preset condition, which can effectively adjust the temperature and save the energy consumption of the device.

In 840-2, in response to a determination that the real-time seawater temperature is not meet the reverse water temperature requirement, and a difference between a current time point and the target time point meets a second preset condition.

The second preset condition may include that the difference between the current time point and the target time point is less than or equal to a preset time interval value. In some embodiments, the preset time interval value may be determined based on historical experience, such as 2 minutes, or the like. In some embodiments, the preset time interval value may be related to the power consumption of a corresponding adjustment device (e.g., compression refrigerator, an absorption refrigerator, and a heat pump) when the power device adjustment is used. For example, the greater the power consumption is, the smaller the preset time interval value may be.

In some embodiments, if the real-time seawater temperature does not meet the reverse water temperature requirement, and the difference between the current time point and the target time point meets the second preset condition, it may indicate that the internal temperature of the shell body may not be adjusted using the seawater flushing adjustment for the abnormal temperature at the target time point, and thus it may be necessary to adjust the internal temperature of the shell body using the power device adjustment in time. The mode of the power device adjustment may not take effect immediately, and it may be necessary to reserve a certain time period for the mode of the power device adjustment to take effect. i.e., the temperature adjustment may be started earlier.

In 840-3, the internal temperature of the shell body may be adjusted by the power device adjustment until the internal temperature of the shell body meets the first preset condition.

In 850, the internal temperature of the shell body that meets the first preset condition may be taken as the initial internal temperature of the shell body, and the internal temperature of the shell body when reaching a target duration may be predicted in combination with the external temperature of the shell body and the target duration through the temperature prediction model.

The initial internal temperature of the shell body may be a corresponding internal temperature of the shell body when the internal temperature of the shell body meets the first preset condition.

The external temperature of the shell body may be the temperature at a position between the shell body and the in-situ filtration device at the corresponding time point when the internal temperature of the shell body meets the first preset condition. The target duration may be a time interval duration between a time point when the internal temperature of the shell body needs to be predicted and an initial time point, and the initial time point may be a corresponding time point when the internal temperature of the shell body meets the first preset condition.

Merely by way of example, the time point when the internal temperature of the shell body meets the first preset condition may be 13:00, the corresponding internal temperature of the shell body at this time point may be 5° C., and the external temperature of the shell body at this time point may be 5.2° C. If the internal temperature of the shell body at 13:40 needs to be predicted, the target duration may be 40 minutes or ⅔ hours.

In some embodiments, the internal temperature of the shell body when reaching the target duration may be predicted by inputting the initial internal temperature of the shell body, the external temperature of the shell body, and the target duration into the temperature prediction model for processing. For more descriptions of the temperature prediction model, please refer to the related contents in FIG. 7.

In 860, it may be determined whether the internal temperature of the shell body exceeds the target temperature range again and the aforementioned operations may be repeated.

The operation in 860 may be similar to the operation in 810. For specific descriptions, please refer to the operation in 810.

In some embodiments, when the filter film holders complete the sampling of the deep-sea microorganism, or it is predicted that the internal temperature of the shell body during the time period before the in-situ filtration device goes out to sea and returns to the researcher is within the target temperature range, the temperature of the shell body may not be predicted, i.e., the operation of determining whether the internal temperature of the shell body exceeds the target temperature range and the subsequent adjustment operation may be terminated.

In some embodiments of the present disclosure, the internal temperature of the shell body when reaching the target duration may be determined by the temperature prediction model, and the temperature adjustment mode for the internal temperature of the shell body may be determined based on the target temperature range, the reverse water temperature requirement, and the second preset condition, so that the internal temperature of the shell body may be adjusted to meet the first preset condition. This process may monitor whether the internal temperature of the shell body reaches the target temperature range in real-time, thereby ensuring that the microorganism may keep active for a long time. Besides, the specific adjustment mode required for temperature adjustment may be determined based on the seawater temperature obtained in real time, so that the adjustment of the internal temperature of the shell body may be effectively performed using the mode of seawater flushing adjustment, thereby ensuring that the internal temperature of the shell body reaches the standard, and saving energy for the device.

It should be noted that the above descriptions of the related solutions are for illustration and description purposes only, and do not limit the scope of application of the present disclosure. Those skilled in the art may make various modifications and alterations under the guidance of the present disclosure. However, such modifications and alterations are still within the scope of the present disclosure.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements, and amendments to the present disclosure. These modifications, improvements, and amendments are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various parts of this specification are not necessarily all referring to the same embodiment. In addition, some features, structures, or features in the present disclosure of one or more embodiments may be appropriately combined.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the present disclosure disclosed herein are illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A large-flux in-situ filtration device for marine microorganism based on a multi-channel circulation distributor, wherein
   the device includes an energy and control module, a circulation distribution module, a filtration module, a pump module, a filtration volume measurement module and a main body support frame;
   the energy and control module includes an electronic compartment and a battery compartment;
   the filtration module includes eight filter film holders;
   the pump module includes a stainless steel gear pump and a deep-sea drive motor;
   the filtration volume measurement module includes a water meter, a camera, and a light emitting diode (LED) light, wherein the filtration volume measurement module measures a volume of filtered seawater using the water meter, and displays the volume of filtered seawater on a dial, when the LED light provides a light source, automatically photographs and records data of the volume of filtered seawater corresponding to each set of samples using the camera; and
   the circulation distribution module includes a multi-channel circulation distributor and a deep-sea servo motor; wherein the multi-channel circulation distributor and the deep-sea servo motor are connected to a shaft sleeve through a coupling; the multi-channel circulation distributor includes a pipe joint, an upper cover plate, a rotor, an outer shell, a spacer column, a transmission connection shaft, a lower cover plate, a polytetrafluoroethylene (PTFE) gasket, and an O-shaped rubber ring;

a center of the upper cover plate is connected to the stainless steel gear pump by the pipe joint, a side of the lower cover plate includes eight pipe joints and an initial sealing position, and the eight pipe joints and the initial sealing position are evenly distributed in a circular array, which are respectively connected to inlets of the filter film holders;

an inside of the rotor is provided with a water passage, one end of the water passage is connected to a central water outlet of the upper cover, and other end of the water passage is sequentially connected to eight water holes inside the lower cover when the rotor rotates for one cycle to realize a connection and sealing of a seawater flow channel;

the upper cover plate, the outer shell, and the lower cover plate are fixed together to form a stator, the rotor is located in an inner space of the stator, the rotor is fastened to the transmission connection shaft, and then connected to the deep-sea servo motor through the coupling, the shaft sleeve is wrapped on an outside of the coupling to fixedly connect the lower cover plate and a shell body of the deep-sea servo motor;

the eight filter film holders of the filter module are distributed around the multi-channel circulation distributor in a circumferential manner, wherein the filter film holders are all stainless steel disc single-layer flat filters, and each of which includes an exhaust valve, set screws, an upper cover plate, a support mesh plate, a lower cover plate, and a bracket; wherein the upper cover plate and the lower cover plate are fixed through the set screws, and the support mesh plate is clamped in the middle, a filter film with a diameter of 142 mm and an aperture of 0.22 μm is placed on the support mesh plate as a pressure support surface of a microporous film, to ensure that the filter film is not liable to break under a filtration pressure;

the stainless steel gear pump of the pump module and the deep-sea drive motor are connected together through the coupling and the shaft sleeve, and a speed of the deep-sea drive motor is adjustable; and an inlet of the stainless steel gear pump is connected to a seawater inlet, an outlet of the stainless steel gear pump is connected to a pipe connection at a center above the multi-channel circulation distributor, and eight pipe connections below a side of the multi-channel circulation distributor are respectively connected to the inlets of the eight filter film holders, and the outlet of each of the filter film holders is connected to an inlet of the water meter through a multi-way pipe joint, and an outlet of the water meter is an outlet of the device.

2. The device of claim 1, wherein
the multi-channel circulation distributor is made of a 316 stainless steel, a joint surface of the rotor and the stator is coated with a corrosion-resistant and wear-resistant material, the outer shell surrounding the rotor is 0.1-0.2 mm higher than the rotor, and a joint surface of the rotor and the upper or lower cover plates is provided with a PTFE spacer column for keeping a space within a range of 0.05-0.1 mm to reduce rotational friction.

3. The device of claim 1, wherein
a seawater channel at a joint face between the rotor and the lower cover plate is sealed with an O-shaped PTFE gasket and the O-shaped rubber ring, wherein the O-shaped rubber ring is located at a bottom of a groove and used for compensating a space at the joint surface using self-elasticity of the O-shaped rubber ring to reduce a seawater leakage; and the PTFE gasket is placed above the O-shaped rubber ring and is close to a surface of the rotor for realizing sliding sealing.

4. The device of claim 1, wherein the deep-sea servo motor realizes a position control through an encoder feedback, so as to complete precise channel switching and connection when driving the rotor to rotate.

5. The device of claim 1, wherein more filter film holders are arranged, and more filter film holders are connected by reducing an angle between adjacent pipe joints on the lower cover plate of the multi-channel circulation distributor and increasing a number of connection joints on the lower cover plate.

6. The device of claim 1, further comprising two pressure sensors, wherein
the two pressure sensors are respectively installed at an inlet and an outlet of the multi-channel circulation distributor, the two pressure sensors are configured to detect a pressure at both ends of the multi-channel circulation distributor, and the energy and control module controls a driving force of the stainless-steel gear pump through the pressure.

7. The device of claim 1, further comprising a temperature-salt-depth sensor, wherein
the temperature-salt-depth sensor is fixed on the main body support frame and connected to the energy and control module using a watertight cable to obtain basic background data of an in-situ sampling.

8. The device of claim 1, further comprising an underwater acoustic communicator, wherein
the underwater acoustic communicator is fixed on the main body support frame, which is connected to the energy and control module with a watertight cable, and the underwater acoustic communicator adopts a serial communication to realize a data transmission between the device and a host computer during a sampling process.

* * * * *